United States Patent
Kenyeres et al.

(10) Patent No.: US 10,519,054 B2
(45) Date of Patent: Dec. 31, 2019

(54) CARRIER INSERT FOR ACCOMMODATING AND MAINTAINING THE BIOFILM CULTURE OF FLUID CLEANING STRUCTURES

(75) Inventors: István Kenyeres, Budapest (HU); Robert Kovács, Budapest (HU)

(73) Assignee: Organica Zartkoruen Mukodo Reszvenytarsasag, Budapest (HU)

( * ) Notice: Subject to any disclaimer, the term of this patent is extended or adjusted under 35 U.S.C. 154(b) by 93 days.

(21) Appl. No.: 13/138,808

(22) PCT Filed: Jan. 13, 2011

(86) PCT No.: PCT/HU2011/000005
§ 371 (c)(1),
(2), (4) Date: Sep. 30, 2011

(87) PCT Pub. No.: WO2011/086398
PCT Pub. Date: Jul. 21, 2011

(65) Prior Publication Data
US 2012/0037551 A1    Feb. 16, 2012

(30) Foreign Application Priority Data
Jan. 13, 2010 (HU) .................... 1000012 U

(51) Int. Cl.
*C02F 3/10*    (2006.01)
(52) U.S. Cl.
CPC .................... *C02F 3/103* (2013.01)
(58) Field of Classification Search
CPC ...... C02F 3/00; C02F 3/04; C02F 3/06; C02F 3/10; C02F 3/101; C02F 3/102;
(Continued)

(56) References Cited

U.S. PATENT DOCUMENTS 3,232,865 A * 2/1966 Quinn et al. .............. 210/610
4,536,988 A * 8/1985 Hogen .................. A01G 31/02
                                                        119/200
(Continued)

FOREIGN PATENT DOCUMENTS

AU    2011206416    7/2011
CA    2786971        2/2017
(Continued)

OTHER PUBLICATIONS

Translation of SU1669872.*
(Continued)

*Primary Examiner* — Peter Y Choi
(74) *Attorney, Agent, or Firm* — Fish & Richardson P.C.

(57) ABSTRACT

The invention relates to a carrier insert for accommodating and maintaining the biofilm culture of fluid cleaning structures, which contains a spatial web made of staple fibres using the hosiery method.

Figure 1:
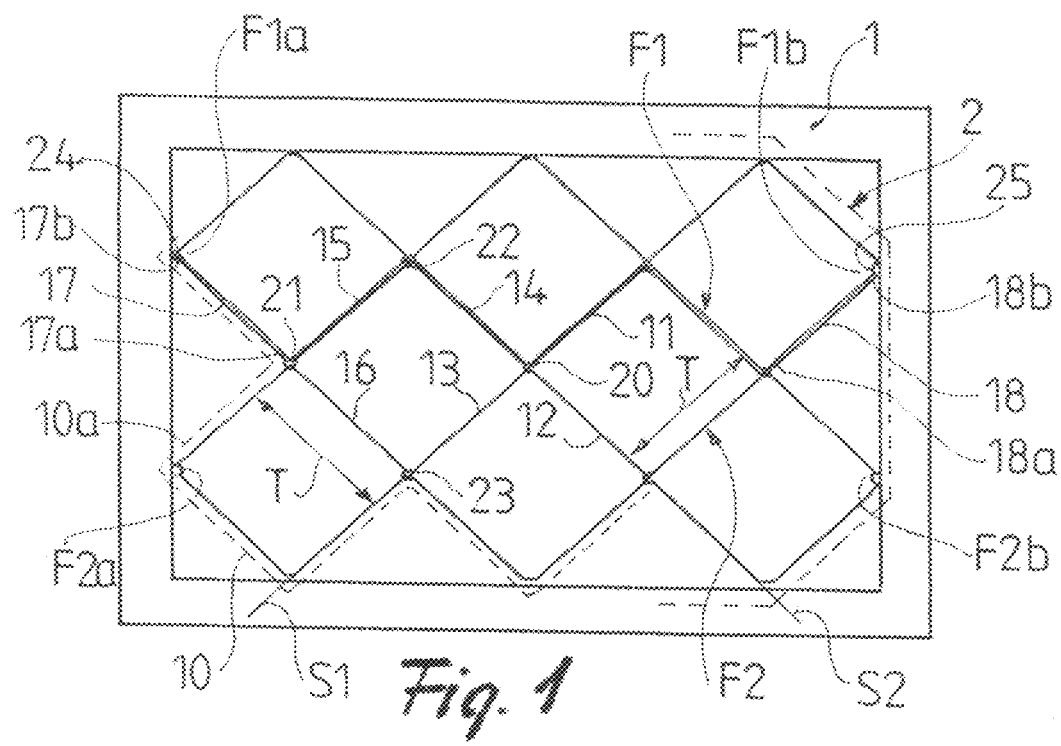

The characteristic feature of the invention is that the web (10) has internal textile units (11, 12, 13, 14, 15, 16) joining each other in intermediate complete nodal points (20, 21, 22, 23) and situated between the complete nodal points (20, 21, 22, 23), and external textile (17, 18) units situated along the edges (10a) of the web (10), where in the case of at least a part of the complete nodal points (20, 21, 22, 23) there is an even number of internal textile units (11, 12, 13, 14, 15, 16) guided into the given complete nodal point (20, 21, 22, 23), the internal sides (17a, 18a) of the external textile units (17, 18) situated along the edges (10a) of the web (10) are connected to a complete nodal point (20, 21, 22, 23) each, and the external sides (17b, 18b) of the external textile units (17, 18) are provided with connection points (24, 25) for (Continued)

joining the structure (1), and via the connection points (24, 25) the web (10) is attached to the structure (1) in a fixed position.

10 Claims, 2 Drawing Sheets

(58) Field of Classification Search
CPC ...... C02F 3/103; C02F 3/109; Y10T 428/236; Y02W 10/15
USPC ..... 442/327; 210/150, 322, 330, 323.1, 348, 210/340, 337
See application file for complete search history.

(56) References Cited

U.S. PATENT DOCUMENTS

| | | | |
|---|---|---|---|
| 4,908,128 | A | 3/1990 | Chiba |
| 6,274,035 | B1 | 8/2001 | Yuan et al. |
| 6,540,920 | B2 * | 4/2003 | Bounds et al. ............... 210/615 |
| 2008/0110827 | A1 | 5/2008 | Cote et al. |
| 2008/0245731 | A1 | 10/2008 | Monosov |

FOREIGN PATENT DOCUMENTS

| | | |
|---|---|---|
| CN | 1530433 | 9/2004 |
| CN | 101367579 | 2/2009 |
| DE | 4233121 | 4/1994 |
| DE | 4233121 A1 | 4/1994 |
| DE | 19730839 A1 | 1/1999 |
| DE | 19730839 | 7/2001 |
| DE | 10143367 | 3/2003 |
| DE | 10143367 A1 | 3/2003 |
| DE | 10132546 | 6/2003 |
| DE | 10132546 C1 | 6/2003 |
| EP | 1234804 | 8/2002 |
| EP | 1234804 A1 | 8/2002 |
| EP | 2523911 | 9/2016 |
| HU | 227984 | 1/2010 |
| JP | 51-149160 U | 5/1950 |
| JP | 46-025070 | 8/1971 |
| JP | 52-089239 | 7/1977 |
| JP | 63-028498 | 8/1988 |
| JP | 03-086100 U | 8/1991 |
| JP | 03-053360 | 11/1991 |
| JP | 06-007898 U | 3/1994 |
| JP | 08-086100 U | 4/1996 |
| JP | 10-099614 | 4/1998 |
| JP | 10-296285 | 11/1998 |
| KR | 10-0893548 | 4/2009 |
| KR | 100893548 | 4/2009 |
| RU | 2011148502 | 1/2011 |
| SG | 10201500244 | 3/2015 |
| SU | 1669872 | 7/1989 |
| UA | 50546 | 10/2002 |
| WO | WO2011/086398 | 7/2011 |

OTHER PUBLICATIONS

International Search Report and Written Opinion issued in PCT application PCT/HU2011/000005 dated May 24, 2011 (10 pages).
International Preliminary Report on Patentability issued in PCT application PCT/HU2011/000005 dated Jul. 26, 2012 (8 pages).
Certificate of Grant in Indian Application No. 2027/MUMNP/2011 dated May 1, 2016.
Certificate of Grant in Indonesian Application No. W00201202852, dated Apr. 25, 2019.
Certificate of Grant in Mexican Application No. MX/u/2012/000302, dated Apr. 21, 2015.
Certificate of Grant in South African Application No. 2012/05664, dated Oct. 30, 2013.
NZ601419 Specification (15 pages).

* cited by examiner

CARRIER INSERT FOR ACCOMMODATING AND MAINTAINING THE BIOFILM CULTURE OF FLUID CLEANING STRUCTURES

The invention relates to a carrier insert for accommodating and maintaining the biofilm culture of fluid cleaning structures, which contains a spatial web made of staple fibres using the hosiery method.

Numerous methods are known for cleaning sewage. One of the best known and most widely used procedures is activated sludge treatment. However, its disadvantage is that the cleaning capacity of the reactors is significantly restricted by the limited biomass retaining ability of activated sludge systems. According to the classic scheme the settling phase following the activated sludge reactor operates favourably as long as the activated sludge concentration inside the reactor remains below a floating matter concentration of 5-6 kg/m$^3$. If the activated sludge concentration inside the reactor is higher than this, greater decomposition capacity can be reached by improving the phase separation step or by fixing it inside the biomass reactor. The option mentioned first is followed for example by membrane separation processes, while the second group of solutions include biofilm reactors.

In the case of biofilm reactors using woven natural or synthetic fibre based textiles as biofilm carriers biofilm development starts on the textile fibres separately too. The condition for this is that the individual fibres must be placed and fixed at an appropriate distance from each other, loosely enough. A significant advantage of this construction is that if the surface of the staple fibres is taken into consideration separately, then a very large specific surface can be coated with biofilm.

A further advantage is that according to experience, if these fibres are used as immersed biofilm carrier elements, biofilm of a very large quantity develops, which has a loose, fibrous structure at the same time, so it is possible to retain a large quantity of biomass without significant limitations of material transfer bearing key importance in the case of biofilm systems.

Several different textile-biofilm carrier solutions focusing on this basic principle became known.

A carrier consisting of vertical load-bearing fixing fibres carrying the weight of the textile and the biofilm settling on the carrier surfaces and of biofilm carrier sections constructed between them in different directions in a way relieved from load bearing is described in patent specification no. DE 101 32 546. At the same time, publication document no. DE 101 43 367 describes further methods for the arrangement of biofilm carrier sections as well as constructions also containing horizontal load-bearing fixing fibres.

Publication document no. US 2008/0245731 relates to a biofilm carrier textile consisting of horizontal load-bearing cross-woven fibres and free fibres connecting them and serving as a biofilm carrier surface.

Patent specification no. DE 197 30 839 relates to a solution, in which the biofilm carrier section does not simply consist of free fibres, but of loops created from such fibres. In this case the carriers are fixed by stiffening rods inserted in separate textile sections to ensure mechanical stability.

A common characteristic feature of the described constructions is that they form spatial structures by stretching the biofilm carrier plates and placing several of these plates next to each other in a parallel position.

Patent specification no. U.S. Pat. No. 6,274,035 describes a biological filter unit constructed from such plates placed close to each other, which solution is based on that the distance between the plates is ensured by distance pieces fitted to the plates themselves. Structures constructed from flat plates are also described in the specification, as well as a solution, where the plates with distance pieces are rolled up into a compact coil to obtain a spatial structure.

Patent specification no. DE 101 32 546 describes a solution, where the individual carriers are provided with a frame each, and then the frames are placed next to each other.

However, the general advantage of the known solutions is that because of the position of the carriers the total surface of the desired size cannot be obtained on the given basic area and the specific performance of the reactor remains below the expectations, or—especially when tubular carriers are used—there is a risk of blocking up, which may result in the reduced operability and reliability of the reactor.

A further disadvantage of the known spatial biofilm carriers is that it is difficult to arrange them to form a spatial structure, and because of the loading of the connections in the nodal points there is an increased risk of failure.

Our aim with the carrier insert according to the invention was to overcome the deficiencies of the known solutions and to create a solution, which has a simple structural construction and enables the creation of a fairly large biofilm carrier surface, while there is not risk of blocking up, controlled flow can be realised and the composition and stretching of the spatial structure does not result in static or mechanical problems in the nodal points.

The constructions according to the invention are based on the recognition that if the textile units created in a way known in itself are connected to each other so that there is always an even number of textile unit endings at the connection points, then it is possible to create the entire spatial structure in a simple way and to fix it easily along its edges, as the forces transferred by the textile units into the nodal points practically "extinguish" each other, and so, without any pulling force or any significant loading of the textile units, the space part bordered by the neighbouring textile units can be kept in the desired form of a channel having an appropriately large cross-section, and so the task can be solved.

In accordance with the set aim, the carrier insert according to the invention for accommodating and maintaining the biofilm culture of fluid cleaning structures—which contains a spatial web made of staple fibres using the hosiery method—, is constructed in such a way that the web has internal textile units joining each other in intermediate complete nodal points and situated between the complete nodal points, and external textile units situated along the edges of the web, where in the case of at least a part of the complete nodal points there is an even number of internal textile units guided into the given complete nodal point, the internal sides of the external textile units situated along the edges of the web are connected to a complete nodal point each, and the external sides of the external textile units are provided with connection points for joining the structure, and via the connection points the web is attached to the structure in a fixed position.

A further criterion of the carrier insert according to the invention is that two of the internal textile units situated in a given complete nodal point are positioned in the same principal plane, and the given principal plane is taken through the given complete nodal point.

In the case of a possible construction of the carrier insert at least a part of the textile units are joined to each other in the complete nodal point with an adhesion and/or cohesion and/or hosiery joint.

In the case of another different version of the invention some of the textile units are made of the same material, and individual groups of such arranged textile units form a main body each.

In the case of a further different realisation of the carrier insert the connection points are situated at the ends of the main bodies or, in a given case, the connection points are placed at the ends of the main bodies and on the free sections between the ends of the main bodies.

From the aspect of the invention it may be favourable, if the distance between the neighbouring complete nodal points is between 50-300 mm, favourably between 100-150 mm.

In the case of a further construction of the carrier insert at least a part of the textile units contain longitudinal free fibres and cross fibres connecting the longitudinal free fibres to each other. Favourably the distance between two neighbouring longitudinal free fibres should be maximum 50 mm, while the distance between two neighbouring cross fibres should be maximum 50 mm, and the cross-section of the longitudinal free fibre (30) should be at least 0.0001 mm$^2$.

The carrier insert construction according to the invention has numerous advantageous features. The most important one of these is that due to the construction and connection of the individual textile units other than the ordinary, the entire spatial structure of the carrier insert can be easily created, the carrier insert can be fitted in the reactor easily and safely, and during use, even after a long period of operation no damage can occur in the nodal points because of the forces deriving from fastening.

A further advantage deriving from this is that the production, operation and maintenance costs of the carrier insert are fairly favourable.

It can also be mentioned as an advantage that due to the spatial structural construction according to the invention—as compared to the known and generally used solutions—the size of the carrier surface situated in a unit of reactor volume can be significantly increased. As a result of this the efficiency of already operating sewage treatment plants can be enhanced without any special reconstruction or any significant cost investment. In the case of new sewage treatment plants, besides a more favourable investment cost a sewage treatment plant of a greater capacity can be built on the same area, or a plant of a given capacity can be realised at a lower cost.

Another advantage is that in the case of using the carrier insert according to the invention the free space used in the reactor appears in the form of channels bordered by an even number of filter units and having a cross-section between 5-30 cm, favourably between 10-15 cm, as a result of which it is possible to realise controlled material flow in the reactor, which results in better mixing and more favourable material transfer, which improves the purification performance of the reactors even more.

It is also regarded as an advantage that because of the carrier insert structure according to the invention, die to the use of the flexible textile units bordering the channels, the risk of blocking up, which is so common in the case of tubular systems, is eliminated, so the operation safety of the construction according to the invention is also much better than in the case of the known tubular solutions.

It can be regarded as the economic advantage of the carrier insert according to the invention that due to the controlled flowing ensured by the specific spatial structure the material transfer inside the reactor improves, the direct advantage of which lies in more perfect oxygen transfer and a lower ventilation demand deriving from it. All this results in saving energy during operation. Due to the elimination of the risk of blocking up—as compared to the use of three-dimensional plastic structures—there is greater operational safety, which, from an economic aspect, is indicated by the reduction of lost operation time deriving from failures caused by blockages.

Figure 3:
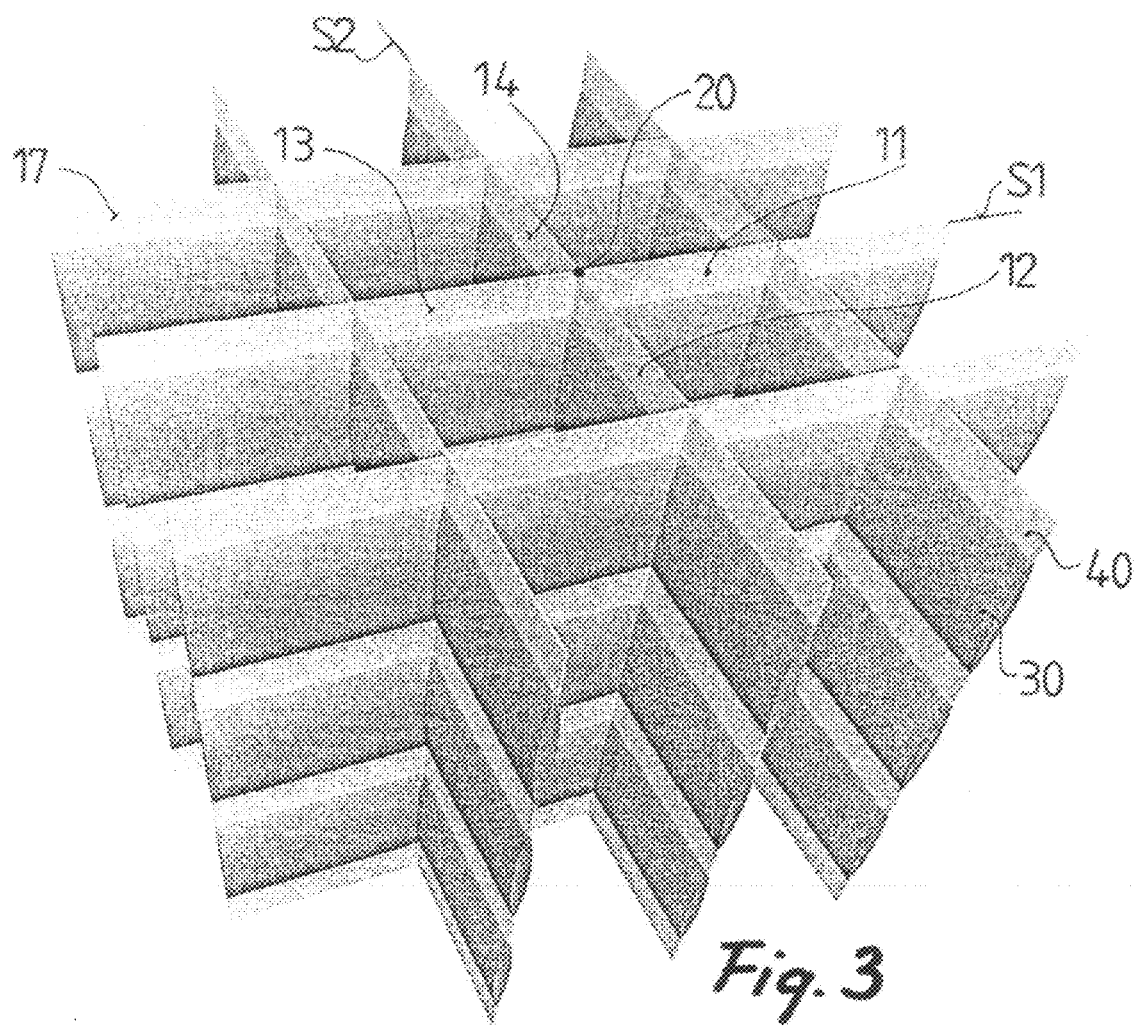
Figure 4:
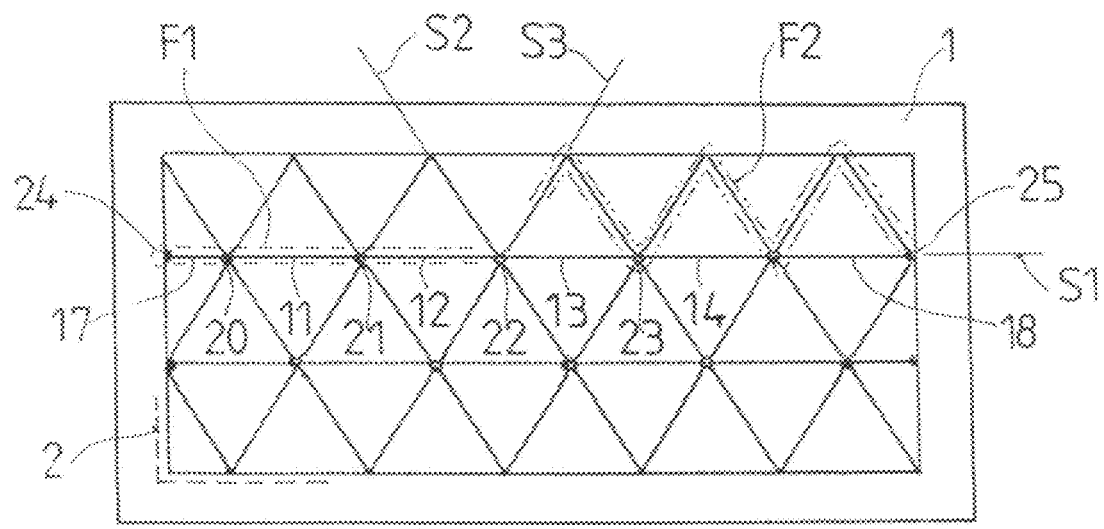

Below the invention is described in detail in connection with construction examples, on the basis of drawings. In the drawings FIG. 1 is the top view of the carrier insert according to the invention, FIG. 2 is the side view of a possible version of the main body used as a building element in the carrier insert as in FIG. 1, FIG. 3 is the schematic view of a version of the carrier insert as in FIG. 1, FIG. 4 is the top view of a further different construction of the carrier insert.

FIG. 1 shows a version of the carrier insert 2 according to the invention, which contains a web 10 placed in the reaction space of the structure 1 for sewage treatment. It can be seen that in the case of this construction of the carrier insert 2 the web 10 is formed by a group of internal textile units 11, 12, 13, 14, 15, 16 joining each other in the complete nodal points 20, 21, 22, 23 and positioned at right angles to their neighbours, and external textile units 17, 18 situated along the edge 10a of the web 10 and joining the structure 1 via connection points 24, 25. In the present case the internal side 17a of the external textile unit 17 is situated in the complete nodal point 21, while its external side 17b touches the structure 1, but the internal side 18a of the external textile unit 18 is situated in a nodal point—not shown in FIG. 1—, while its external side 18b is situated along the bordering structure 1. In this arrangement the web 10 borders tubes of the shape of a rectangular prism, where distance "T" between complete nodal point 20 and complete nodal point 22, complete nodal point and complete nodal point 21, complete nodal point 21 and complete nodal point 23, and finally between complete nodal point 23 and complete nodal point 20 is of the same size. Practically distance "T" is between 50-300 mm, but favourably distance "T" is between. 100-150 mm.

Figure 2:
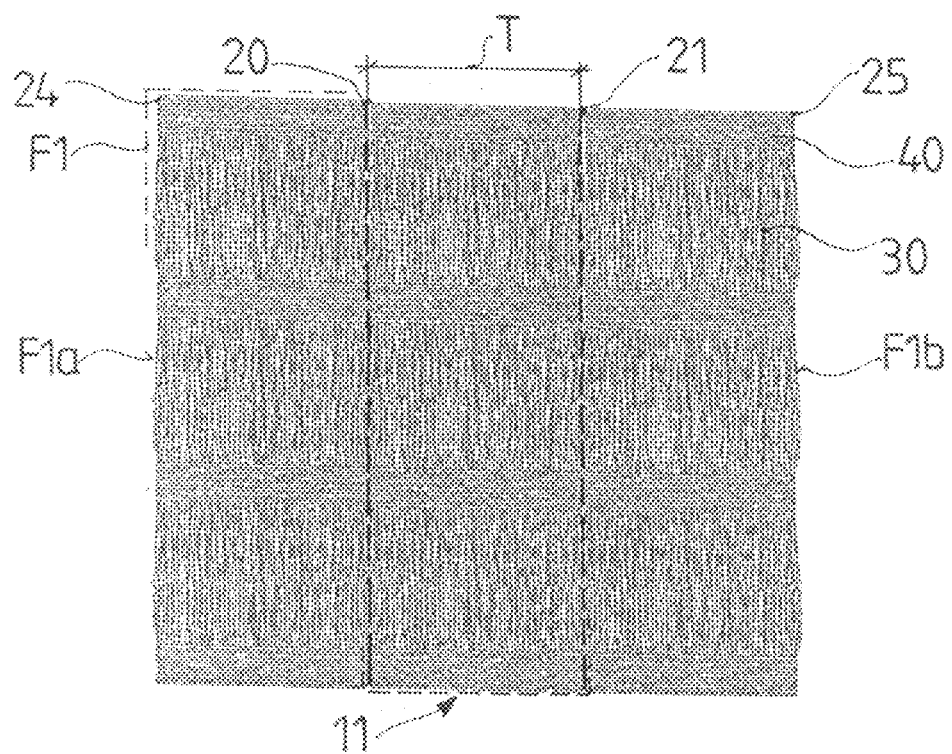

The individual internal textile unit 11, 12; 13, 14, 15, 16, and also the external textile units 17, 18—as shown in FIG. 2—consist of cross fibres 40 and longitudinal free fibres 30. Practically the longitudinal free fibres 30 are situated loosely beside each other in the vertical direction of the internal textile unit 11, while the density of the cross fibres 40 is much greater. In the part strengthened with cross fibres 40 the distance between two neighbouring cross fibres 40 is maximum 50 mm, while the cross-section of the longitudinal free fibres 30 loosely hanging next to each other is at least 0.0001 mm$^2$.

In FIG. 1 it can be seen that the group of several textile units situated next to each other, such as for example external textile unit 17, internal textile unit 15, internal textile unit 14, internal textile unit 11 and further textile units form the main body "F1". The very top section—horizontal in FIG. 2—of main body "F1" strengthened with cross fibres 40 is suitable for assuming the force needed for fastening the main body "F1" to the structure 1 and transfer it between the one end "F1a" and the other end "F1b" of the main body "F1".

FIG. 1 also shows that in the individual nodal points, for example in complete nodal point 20, among the internal textile units 11, 12, 13, 14 belonging here, internal textile unit 11 and internal textile unit 13 are situated in the same principal plane "S1", while internal textile unit 12 and internal textile unit 14 are also situated in the same principal plane "S2". As a result of this, in the fastened position of the carrier insert 2 minimal lateral force is generated in complete nodal point 20.

It can also be seen in FIG. 1 that the main body "F1" is folded up along a zigzag line, so that in the case of the neighbouring external textile unit 17, internal textile unit 15, internal textile unit 14, internal textile unit 11 and the further textile units the complete nodal point 21, complete nodal point 22 and complete nodal point 20 are in contact with the neighbouring main bodies "F2" on the two sides of main body "F1". In this way, in complete nodal point 20 the internal textile unit 14 and the internal textile unit 11 of main body "F1" consisting of the same material, and the internal textile unit 13 and the internal textile unit 12 of main body "F2" consisting of the same material are attached to each other.

The connection of main body "F1" and main body "F2" in the complete nodal point 20 can be solved with an adhesion, cohesion or other mechanical joint, e.g. sewing, in complete nodal point 20. Obviously the web 10 having a square grid pattern in top view can be created by proceeding in a similar way in the case of all nodal points of the carrier insert 2. It is obvious that the main body "F2" is also attached to the structure 1 at its "F2a" and at its "F2b" end. The main body arranged along the structure—as shown in FIG. 1—joins the structure 1 at several corner points between the ends.

FIG. 3 shows the position of a part of the web 10. The complete nodal point 20 and the internal textile units 11, 12, 13, 14 joining here can be seen again, where the internal textile unit 11 and the internal textile unit 13 are situated in principal plane "S1", while the internal textile unit 12 and the internal textile unit 14 are situated in principal plane "S2". The structure of the individual internal textile units 11 and external textile units 17 can also be seen, which consists of horizontal cross fibre 40 sections running parallel to each other and a set of vertical longitudinal free fibres 30.

FIG. 4 shows the top view of another version of the carrier insert 2 according to the invention. Here a part of the main bodies, e.g. main body "F1" consists of internal textile units 11, 12, 13, 14 running in one single straight principal plane "S1" and the external textile unit 18. At the same time, between two straight main bodies "F1" there are main bodies "F2" folded up along a zigzag line, which join the main bodies "F1" in complete nodal points 20, 21, 22, 23. In the case of this construction, in the complete nodal points, for example in nodal point 20, there six internal textile units meeting each other, always of an even number, so the generated forces affecting the given complete nodal point 20 are minimal here too, as two internal textile units are situated in principal plane "S1", another two in principal plane "S2", and the last two in principal plane "S3". The plane where the forces exert their effect and the absolute value of the forces is the same, but the forces have opposite directions, so practically they extinguish each other.

When producing the carrier inserts 2 according to the invention first of all the main bodies "F1" are created and their neighbouring main bodies "F2", using the hosiery method known in itself, so that only at given larger distances are the longitudinal free fibres 30 held together by the neatly arranged bands of more densely woven cross fibres 40. In the following the finished main bodies "F1" and main bodies "F2" are fastened to each other in the appropriate complete nodal points 20 suiting their required position, and in this way the neatly arranged spatial structure of the internal textile units 11, 12, 13, 14, 15, 16 and the external textile units 17, 18 is created. Finally this structure is fastened to the structure 1 via the connection points 24, 25 of the external textile units 17, 18, so that the individual internal textile units 11, 12, 13, 14, 15, 16 and the external textile units 17, 18 extend into the reactor space.

Even when these carrier inserts 2 are used, the sewage is purified in the ordinary way, but due its soft structure the carrier insert 2 according to the invention forms a significantly larger biofilm carrier surface, it does not get blocked, and it also enables controlled sewage flow.

The carrier insert according to the invention can be favourably used in sewage treatment plants using biofilm.

LIST OF REFERENCES 1 structure
2 carrier insert
10 web 10a edge
  11 internal textile unit
  12 internal textile unit
  13 internal textile unit
  14 internal textile unit
  15 internal textile unit
  16 internal textile unit
  17 external textile unit
  17a internal side
  17b external side
  18 external textile unit
  18a internal side
  18b external side
20 complete nodal point 21 complete nodal point
  22 complete nodal point
  23 complete nodal point
  24 connection point
  25 connection point
30 longitudinal free fibre
40 cross fibre
"F1" main body "F1a" end
  "F1b" end
"F2" main body "F2a" end
  "F2b" end
"S1" principal plane
"S2" principal plane
"S3" principal plane
"T" distance

The invention claimed is:

1. An apparatus for sewage treatment, the apparatus comprising
   a sewage reactor structure including four sides having four corresponding internal faces arranged in a rectangle and enclosing a reaction space within the reactor structure in which flowing sewage is to be processed, and
   a spatial web (1) made of staple fibres, and (2) having connection points attached to and stretched between the four sides of the sewage reactor structure in four different directions, two of the four directions of stretching being opposed to one another and parallel to two of the four sides of the sewage reactor structure and the other two of the four directions of stretching being opposed to one another and parallel to the other two of the four sides of the sewage reactor structure, to form a carrier insert within the reaction space, the spatial web configured to carry a biofilm culture, the carrier insert formed by the stretching and attachment of the spatial web being in a stationary position and having channels through which the sewage is to flow within the reactor structure, wherein:

(a) the spatial web has internal flexible vertical textile units joining each other in intermediate complete nodal points and situated between the intermediate complete nodal points, and external textile units situated along edges of the spatial web, (b) in the case of at least a part of the intermediate complete nodal points internal flexible textile units of three pairs of internal flexible textile units are guided into each of the intermediate complete nodal points, the textile units and complete nodal points forming the channels through which the sewage is to flow, each of the channels being of triangular cross-section, (c) each of the internal sides of external textile units situated along the edges of the web is connected to a respective one of the intermediate complete nodal points, (d) external sides of the external textile units of the spatial web are provided with the connection points configured to be attached to cause the spatial web to stretch and to form the carrier insert in the stationary position within the enclosed reaction space of the stationary structure, and with the nodal points in stationary positions in the carrier insert, (e) the two of the internal textile units of each of the three pairs of internal textile units situated in a given intermediate complete nodal point are positioned in a same principal plane, the principal plane being taken through the given intermediate complete nodal point, each side of each of the internal flexible textile units being parallel to the principal plane, and (f) at least one of the external textile units and at least one of the internal textile units form a single straight principal main body extending continuously from one of the connection points attached to one side of the sewage reactor structure to another one of the connection points attached to the opposite side of the sewage reactor structure.

2. The apparatus as recited in claim 1, wherein at least a part of the internal and external textile units are joined to each other in the given complete nodal point with one of an adhesion, a cohesion, sewing, or other mechanical joint.

3. The apparatus as recited in claim 2, wherein some of the internal and external textile units are made of a same material, and individual groups of said internal and external textile units each form a main body.

4. The apparatus as recited in claim 3, wherein the connection points are situated at ends of the main bodies.

5. The apparatus as recited in claim 3, wherein the connection points are placed at ends of the main bodies and on free sections between the ends of the main bodies.

6. The apparatus as recited in claim 3, wherein a distance (T) between neighboring complete nodal points is in a range of 50-300 mm.

7. The apparatus as recited in claim 6, wherein at least a part of the internal and external textile units contain longitudinal free fibres and cross fibres connecting the longitudinal free fibres to each other.

8. The apparatus as recited in claim 7, wherein a distance between two neighboring longitudinal free fibres is no greater than 50 mm.

9. The apparatus as recited in claim 7, wherein a distance between two neighboring cross fibres is no greater than 50 mm.

10. The apparatus as recited in claim 7, wherein a cross-section of the longitudinal free fibres is at least $0.0001$ mm$^2$.

* * * * *

UNITED STATES PATENT AND TRADEMARK OFFICE
CERTIFICATE OF CORRECTION

PATENT NO. : 10,519,054 B2  
APPLICATION NO. : 13/138808  
DATED : December 31, 2019  
INVENTOR(S) : István Kenyeres and Robert Kovács Page 1 of 1

It is certified that error appears in the above-identified patent and that said Letters Patent is hereby corrected as shown below:

In the Claims

Column 7, Line 28, Claim 1, after "the" delete "enclosed".

Signed and Sealed this
Twelfth Day of May, 2020

Andrei Iancu
*Director of the United States Patent and Trademark Office*